United States Patent
Shimizu et al.

(10) Patent No.: US 9,519,830 B2
(45) Date of Patent: Dec. 13, 2016

(54) OPHTHALMOLOGIC IMAGE PROCESSING METHOD AND STORAGE MEDIUM STORING PROGRAM FOR EXECUTING THE METHOD

(71) Applicant: NIDEK CO., LTD., Aichi (JP)

(72) Inventors: Kazunari Shimizu, Aichi (JP); Yukinobu Ban, Aichi (JP); Tetsuya Yamamoto, Aichi (JP)

(73) Assignee: NIDEK CO., LTD., Aichi (JP)

( * ) Notice: Subject to any disclaimer, the term of this patent is extended or adjusted under 35 U.S.C. 154(b) by 140 days.

(21) Appl. No.: 14/610,058

(22) Filed: Jan. 30, 2015

(65) Prior Publication Data

US 2015/0221125 A1    Aug. 6, 2015

(30) Foreign Application Priority Data

Feb. 3, 2014 (JP) .................................. 2014-018716

(51) Int. Cl.
| | |
|---|---|
| *G06K 9/00* | (2006.01) |
| *A61B 3/10* | (2006.01) |
| *A61B 3/00* | (2006.01) |
| *A61B 3/103* | (2006.01) |
| *A61B 3/107* | (2006.01) |
| *A61B 3/11* | (2006.01) |
| *A61B 3/14* | (2006.01) |
| *A61B 3/117* | (2006.01) |

(52) U.S. Cl.
CPC .......... *G06K 9/0061* (2013.01); *A61B 3/0025* (2013.01); *A61B 3/10* (2013.01); *A61B 3/103* (2013.01); *A61B 3/1005* (2013.01); *A61B 3/107* (2013.01); *A61B 3/1015* (2013.01); *A61B 3/112* (2013.01); *A61B 3/14* (2013.01); *A61B 3/117* (2013.01); *G06T 2207/30041* (2013.01)

(58) Field of Classification Search
None
See application file for complete search history.

(56) References Cited

U.S. PATENT DOCUMENTS

| | | | | |
|---|---|---|---|---|
| 5,574,473 | A | * 11/1996 | Sekiguchi | ............ A61B 3/113 345/32 |
| 5,907,388 | A | 5/1999 | Fujieda | |
| 7,374,286 | B2 | * 5/2008 | Fujieda | ............ A61B 3/1015 351/205 |

(Continued)

FOREIGN PATENT DOCUMENTS

| | | |
|---|---|---|
| JP | 10108837 A2 | 4/1998 |
| JP | 2006026242 A2 | 2/2006 |

(Continued)

*Primary Examiner* — Utpal Shah
(74) *Attorney, Agent, or Firm* — Rankin, Hill & Clark LLP

(57) ABSTRACT

An ophthalmic image processing method includes: acquiring information about characteristics of an examinee's eye including corneal information about the corneal anterior surface shape of the examinee's eye, and refractivity information about refraction of the examinees eye as a whole; generating a simulation image of a target image formed at fundus of the examinee's eye using the refractivity information; and simultaneously displaying an eyeball model image showing an eyeball structure, the simulation image, and a corneal information image associated with the cornea on the eyeball model image and corresponding to the corneal information.

17 Claims, 4 Drawing Sheets

(56) References Cited

U.S. PATENT DOCUMENTS

| | | | |
|---|---|---|---|
| 2005/0225724 A1* | 10/2005 | Klyce | A61B 3/107 351/212 |
| 2009/0180073 A1* | 7/2009 | Ichikawa | A61B 3/14 351/208 |
| 2010/0082017 A1* | 4/2010 | Zickler | A61F 9/00834 606/4 |
| 2012/0120368 A1* | 5/2012 | Fujimora | A61B 3/102 351/206 |
| 2013/0128226 A1* | 5/2013 | Yahagi | A61B 3/12 351/206 |
| 2014/0307228 A1* | 10/2014 | Ohban | A61B 3/12 351/208 |
| 2014/0313480 A1* | 10/2014 | Ohta | A61B 3/10 351/206 |
| 2015/0010226 A1* | 1/2015 | Kubota | A61B 3/102 382/131 |
| 2015/0371383 A1* | 12/2015 | Chabrier | A61B 3/12 600/427 |

FOREIGN PATENT DOCUMENTS

| | | | |
|---|---|---|---|
| JP | 2010201072 A2 | 9/2010 | |
| JP | 2013236902 A2 | 11/2013 | |

\* cited by examiner

OPHTHALMOLOGIC IMAGE PROCESSING METHOD AND STORAGE MEDIUM STORING PROGRAM FOR EXECUTING THE METHOD

CROSS-REFERENCE TO RELATED APPLICATION

This application claims priority from Japanese Patent Application No. 2014-018716 filed with the Japan Patent Office on Feb. 3, 2014, the entire content of which is hereby incorporated by reference.

BACKGROUND

1. Technical Field

The present disclosure relates to an ophthalmic image processing method for displaying characteristics of an examinee's eye obtained by an optometry apparatus, and a storage medium having a program for executing the method stored therein.

2. Description of the Related Art

Conventionally, a device is known that integrally displays images showing information about characteristics of various locations of an examinee's eye that are obtained by an optometry apparatus. For example, in a device described in JP-A-2010-201072, a wavefront aberration analysis map and a corneal anterior surface shape analysis map are simultaneously displayed.

There is also known a device that simulates, using software, how a target image appears to the examinee's eye of which a refractive error is corrected with an eyeglass lens and the like, based on the wavefront aberration data of the examinee's eye. For example, JP-A-2013-236902 discloses simulation about the way a target image appears to the examinee's eye wearing an intraocular lens.

SUMMARY

An ophthalmic image processing method includes: acquiring information about characteristics of an examinee's eye including corneal information about the corneal anterior surface shape of the examinee's eye, and refractivity information about refraction of the examinee's eye as a whole; generating a simulation image of a target image formed at fundus of the examinee's eye using the refractivity information; and simultaneously displaying an eyeball model image showing an eyeball structure, the simulation image, and a corneal information image associated with the cornea on the eyeball model image and corresponding to the corneal information.

DESCRIPTION OF THE EMBODIMENTS

Figure 1:
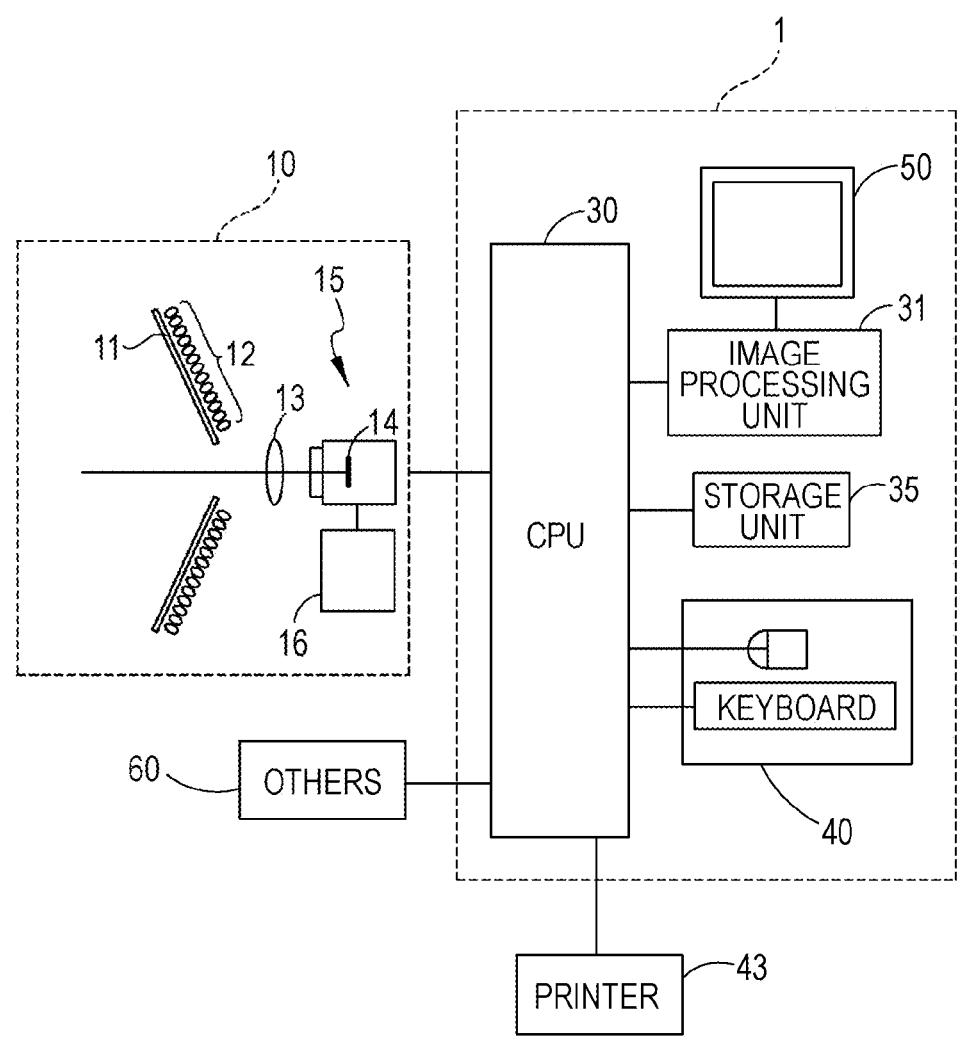
FIG. 1 is a block diagram of the overall configuration of an ophthalmic information processing device according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

However, in the device described in JP-A-2010-201072, images showing information about the characteristics of various locations are simply arranged on the screen. In the device described in JP-A-2013-236902, simulation images and the like are simply arranged on the screen. Thus, in these devices, it may be difficult for a person not familiar with examinations to understand the information and/or images.

An object of an embodiment of the present disclosure is to provide an ophthalmic image processing method for enabling information and/or an image to be displayed in a readily and intuitively understandable manner, and a storage medium having a program for executing the method stored therein.

An ophthalmic image processing method according to an embodiment of the present disclosure includes: acquiring information about characteristics of an examinee's eye including corneal information about the corneal anterior surface shape of the examinee's eye, and refractivity information about refraction of the examinee's eye as a whole; generating a simulation image of a target image formed at fundus of the examinee's eye using the refractivity information; and simultaneously displaying an eyeball model image showing an eyeball structure, the simulation image, and a corneal information image associated with the cornea on the eyeball model image and corresponding to the corneal information.

A non-transitory storage medium according to an embodiment of the present disclosure having a computer program for causing a computer to function as an ophthalmic information processing device stored therein, the ophthalmic information processing device performs: acquiring information about the characteristics of an examinee's eye including corneal information about a corneal anterior surface shape of the examinee's eye and refractivity information about refraction of the examinee's eye as a whole; generating a simulation image of a target image formed at the fundus of the examinee's eye using the refractivity information; and simultaneously displaying an eyeball model image showing an eyeball structure, the simulation image, and a corneal information image associated with the cornea on the eyeball model image and corresponding to the corneal information.

According to an embodiment of the present disclosure, information and/or an image can be displayed in an easily and intuitively understandable manner.

In the following, an embodiment of the present disclosure will be described with reference to the drawings. First, with reference to FIG. 1, the overall configuration of an ophthalmic information processing device 1 that executes an ophthalmic information processing program according to the present embodiment will be described. According to an embodiment of the present disclosure, an ophthalmic image processing method which will be described later may be implemented by having the ophthalmic information processing program executed by a processor of the ophthalmic information processing device 1.

The ophthalmic information processing device 1 (hereafter simply referred to as "the processing device 1") according to the present embodiment simulates the way a target image appears to the examinee's eye by processing information about refraction of the examinee's eye. As a result, a simulation image concerning the way the target image appears is generated. While the details will be described later, the simulation image may include an image showing the way the target image appears to the examinee's eye of which refractive error is corrected, as well as an image showing the way the target image appears to the naked eye. The processing device 1 according to the present embodiment outputs, besides the simulation image, characteristics information images (such as a corneal anterior surface shape analysis map, an aberration map, and a retro-illumination image) showing information that the examinee's eye has concerning the characteristics of an eye optical system. While the details will be described later, the processing device 1 according to the present embodiment further displays am eyeball model image showing the structure of the eyeball so that the relevance between the simulation image and the characteristics information images can be intuitively known.

In the present embodiment, the processing device 1 is provided with a CPU (operating and processing unit) 30, a storage unit (memory) 35, an operation input unit (hereafter referred to as an input unit) 40, a monitor 50, and an image processing unit 31. These units are mutually connected via a bus and the like. To the processing device 1 (CPU 30), a printer 43 is connected.

The CPU 30 is a processor (a computer or a part thereof) that controls the operation of the various units in accordance with a program. The input unit 40 is an input device operated by an examiner. Examples of the input unit 40 include a switch, a keyboard, and a pointing device (such as a mouse and touch panel). The image processing unit 31 performs various image processes on the basis of a command from the CPU 30. The image processing unit 31 also displays various images and the like on a display screen of the monitor 50 on the basis of a command from the CPU 30. The storage unit 35 stores various programs executed by the CPU 30, for example. An ophthalmic information processing program which will be described later is also stored in the storage unit 35. Examples of the storage unit 35 include a semiconductor memory, a magnetic storage device, and an optical storage device. The monitor 50 is used as an output device (display device) and controlled by the CPU 30. The monitor 50 according to the present example is a touch panel enabling an input operation by the examiner, and includes the function as the input unit 40.

The ophthalmic information processing program and various programs may be recorded in a non-transitory, computer-readable recording medium ("recording medium"), such as an optical disk, a magnetooptic disk, a magnetic disk, or a flash memory. The programs may also be provided via an information communication line, such as the Internet.

To the processing device 1, there may be connected an optometry apparatus for obtaining information about the characteristics of the examinee's eye (hereafter referred to as "characteristics information"). For example, in the present embodiment, mainly an anterior segment measuring apparatus 10 is connected to the processing device 1. The processing device 1 and the anterior segment measuring apparatus 10 may have separate housings. In this case, a general-purpose computer capable of executing the ophthalmic information processing program (such as a PC) may be used as the processing device 1. The processing device 1 and the anterior segment measuring apparatus 10 may be integrated. In this case, the CPU 30 of the processing device 1 may be configured to control the various units of the anterior segment measuring apparatus 10.

The anterior segment measuring apparatus 10 is used for measuring optical parameters in the anterior segment (including the cornea, the iris, the crystalline lens, and the like). For example, the anterior segment measuring apparatus 10 according to the present embodiment irradiates the cornea of the examinee's eye with measurement light and receives reflected light to measure the shape of the cornea (including, at least, the shape of the corneal anterior surface) of the examinee's eye. The corneal anterior surface shape data obtained by the anterior segment measuring apparatus 10 is analyzed to provide various information about the shape of the corneal anterior surface, such as refraction data (for example, refractivity distribution), curvature data (for example, curvature distribution), and three-dimensional shape data and aberration data (such as aberration map data and high-order aberration map data).

Hereafter, the anterior segment measuring apparatus 10 according to the present embodiment will be described as a device for measuring optical parameters in the anterior segment (such as the shape of the corneal anterior surface) by projecting a placido target onto the cornea of the examinee's eye and receiving the reflected light. In another embodiment, the anterior segment measuring apparatus 10 may include a device that measures the optical parameters in the anterior segment using an optical interference principle (anterior segment optical coherence tomography).

The anterior segment measuring apparatus 10 in the present example includes a placido plate 11, an illumination light source 12, an anterior segment imaging optical system 15, and a control unit 16. In the placido plate 11, a number of placido rings are formed. The illumination light source 12 illuminates the ring patterns of the placido plate 11 substantially uniformly with respect to the examinee's eye. The anterior segment imaging optical system 15 includes a photography lens 13 and a two-dimensional imaging element 14. The anterior segment imaging optical system 15 captures a ring pattern image projected on the cornea of the examinee's eye using the two-dimensional imaging element 14. The ring pattern image is analyzed to obtain information about the shape of the corneal anterior surface.

In the present embodiment, the anterior segment imaging optical system 15 captures an anterior segment image including the pupil portion of the examinee's eye. From the anterior segment image, the pupil diameter of the examinee's eye is measured, for example. The anterior segment measuring apparatus 10 may be configured to image the examinee's eye while switching the amount of illuminating light. For example, the anterior segment imaging optical system 15 may capture the anterior segment image of the examinee's eye in each of photopic vision and twilight vision. In this case, the illumination light source 12 may be configured such that its output (the amount of light) is adjustable to a first illumination light amount for photopic vision photography and a second illumination light amount for twilight vision photography which is smaller than the first illumination light amount.

The anterior segment measuring apparatus 10 according to the present embodiment is further provided with a measuring optical system (such as the phase difference system disclosed in JP-A-10-108837, or an eye aberration meter using a Shack-Hartmann sensor), which is not shown. The measuring optical system measures refraction data, wavefront data and the like of the examinee's eye as a whole by projecting a measurement light flux onto the examinee's eye and receiving fundus reflected light from the measurement light flux.

The anterior segment measuring apparatus 10 may be configured to capture an inner-pupil image (a so-called retro-illumination image) of the examinee's eye. For example, the anterior segment measuring apparatus 10 projects illuminating light into the pupil of the examinee's eye by switching on a measuring light source of a measuring optical system that measures the refraction data and wavefront data and the like of the examinee's eye as a whole. The anterior segment measuring apparatus 10 further produces an image projected on an imaging element, which is not shown, using fundus reflected light obtained as the illuminating light is reflected by the fundus. Thus, a retro-illumination image is captured.

The processing device 1 and the anterior segment measuring apparatus 100 are connected by a LAN and the like. Thus, the information obtained by the anterior segment measuring apparatus 10 is transferred to the storage unit 35 of the processing device 1.

The processing device 1 is connectable with an ophthalmic apparatus 60 (such as an ocular axial length measuring apparatus or optical coherence tomography) other than the anterior segment measuring apparatus 10. Thus, the processing device 1 can obtain characteristics information which is difficult to obtain with the anterior segment measuring apparatus 10 (such as ocular axial length data and cross section image data of the cornea or the fundus).

With reference to the flowchart of FIG. 2, an example of the process performed by the processing device 1 by having the ophthalmic information processing program executed by the CPU 30 will be described.

First, in an eye information acquisition process (S1: acquisition step), characteristics information of the examinee's eye is acquired by the processing device 1. The characteristics information obtained by the process of S1 includes corneal information about the anterior surface shape of the cornea of the examinee's eye and refractivity information. The corneal information includes, for example, the corneal anterior surface's three-dimensional shape data, curvature data, refraction data, and aberration data. The refractivity information is information about refraction of the examinee's eye as a whole, and includes, for example, refraction data and aberration data.

In the present embodiment, there is further obtained intraocular information as characteristics information. The intraocular information includes at least one of information about the opacity in the examinee's eye, and information about refraction in the examinee's eye except for the corneal ante or surface. The intraocular information includes, for example, information indicating the degree of opacity in the examinee's eye, and refraction data and aberration data in the examinee's eye except for the corneal anterior surface. Size information about the examinee's eye (such as pupil diameter data and ocular axial length data) may be acquired as characteristics information. The characteristics information may be in the form of a result of measurement of the examinee's eye by the optometry apparatus (such as the anterior segment measuring apparatus 10), or image data of an image captured by the optometry apparatus (such as an anterior segment image, a ring pattern age, or a retro-illumination image).

While details will be described later, in the present embodiment, the characteristics information acquired by the process of S1 (more specifically, the refractivity information of the examinee's eye as a whole) is utilized to generate a simulation image showing the way a target image appears to the examinee's eye (see S3). The characteristics information obtained by the process of S1 is also utilized to display the characteristics information image of the examinee's eye (see S4).

In the present embodiment, the process of S1 will be described as a process of transferring the measurement result and images and the like obtained by the optometry apparatus connected to the processing device 1 to the storage unit 35 and the like. However, the process content is not necessarily limited to the above. For example, the process of S1 may include a process of feeding the measurement result and the like of the examinee's eye obtained by the optometry apparatus and stored in an external storage device to the storage unit 35. The process of S1 may also include a process of obtaining, as characteristics information, a result of analysis (analysis result) of the measurement result and the like obtained by the optometry apparatus. Obviously, the process of S1 may include a process combining the above processes.

In a correction data acquisition process (S2: correction data acquisition step), correction data of a corrective lens for correcting the refractive error of the examinee's eye is acquired by the processing device 1. In the present embodiment, a case will be described in which the corrective lens is an eyeglass lens. The corrective lens, however, may be a contact lens or an intraocular lens and the like. The correction data may include, for example, actual lens meter data; a measurement result by an auto refractometer, a wavefront sensor and the like; a subjective examination result; or an examiner input value. The correction data may further include information about the distance from the examinee to the target (use distance information), or information (lens placement interval information) about the interval between the examinees eye and the corrective lens (corrective lens placement interval). Hereafter, the process of S2 will be described as a process of the CPU 30 acquiring, as correction data, lens parameters (such as the values of S (spherical diopter power), C (cylindrical diopter power), and A (astigmatic axial angle)) that are input by an input operation by the examiner using the input unit 40. The process of S2 is not necessarily limited to the above. For example, the process of S2 may include a process of the processing device 1 receiving correction data from the ophthalmic apparatus, an external storage device and the like connected to the processing device 1.

The correction data acquired by the process of S2 are utilized, together with the refractivity information of the examinee's eye, for generating a simulation image. The processing device 1 according to the present embodiment may be configured to generate the simulation in age of the target image formed at the fundus of the examinees eye wearing a corrective lens (a wearing simulation image). The processing device 1 may also be configured to generate the simulation image of the target image formed at the fundus of the naked eye (non-wearing simulation image). For example, the non-wearing simulation mage may be generated when the spherical diopter power S and the cylindrical diopter power C of the correction data are 0 (D), or when an instruction for performing simulation in the naked eye state is received via the input unit 40.

Figure 2:
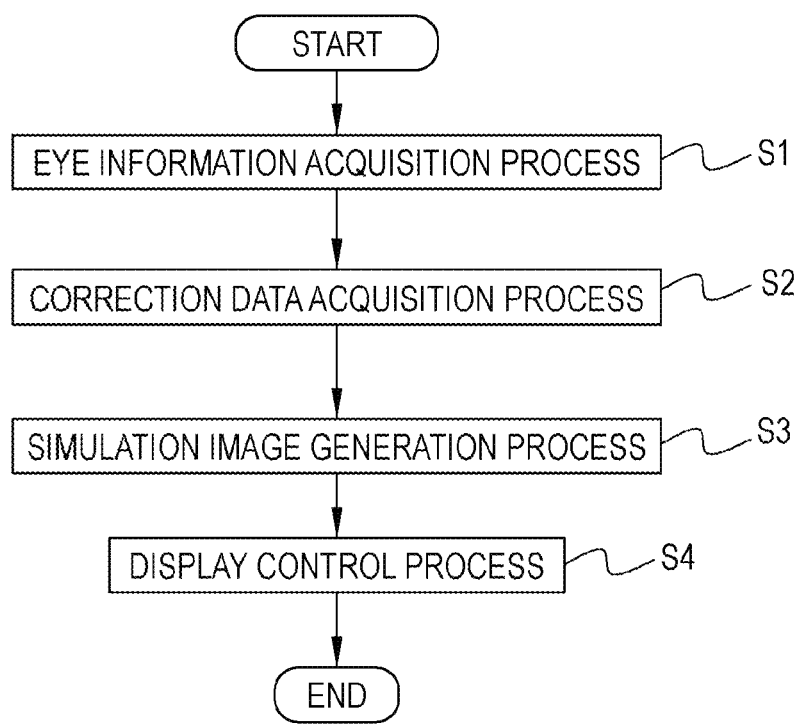
FIG. 2 is a flowchart of the flow of processing by an ophthalmic information processing program.

Then, in the flowchart of FIG. 2, a simulation image generating process (S3: generating step) is executed by the CPU 30. In the process of S3, the CPU 30 generates the simulation image on the basis of at least the refractivity information of the examinee's eye as a whole acquired by the process of S1 (S3). The simulation image represents the target image formed at the fundus (retina) of the examinee's eye. Namely, the way the target image appears to the examinee's eye is shown by the simulation image.

In the process of S3, the simulation image may be generated using various targets. For example, in the present embodiment, there are generated a first simulation image 105 showing the way one or a plurality of subjective examination targets (such as a visual acuity examination target, an astigmatism target, and a screening target) appear, and a second simulation image 106 showing the way a point image (point target) appears (see FIG. 3). The first simulation image 105 is obtained by a simulation sing a subjective examination target (first target). The second simulation image 106 is obtained by a simulation using a point image (second target).

The second simulation image 106 may be an image two-dimensionally showing a point image strength distribution (PSF) obtained by subjecting the wavefront aberration of the examinee's eye to Fourier transform. The first simulation image 105 is obtained, for example, by multiplying an optical transfer function (OTF) obtained by further Fourier transform of the point image strength distribution (PSF) with the space frequency distribution of the subjective examination target.

In the present embodiment, the corrective lens correction data acquired by the process of S2 is incorporated into simulation. In this case, as the simulation images 105 and 106, the above-described wearing simulation image is generated using at least the correction data and the refractivity information of the examinee's eye. The wearing simulation image is a simulation image of the target image formed at the fundus of the examinee's eye wearing a corrective lens. In the process of S3, the non-wearing simulation image may be generated as the simulation images 105 and 106. The non-wearing simulation image is a simulation image of the target image formed at the fundus of the examinee's eye not wearing a corrective lens (i.e., of the naked eye). The non-wearing simulation image is generated using at least the refractivity information of the examinee's eye.

Further, in the present embodiment, as the effective pupil diameter used for simulation, the pupil diameter of the examinee's eye in photopic vision and the pupil diameter of the examinee's eye in twilight vision are used. Which of the two types of pupil diameters are used may be determined in accordance with the examinee's eye environment during simulation. More specifically, when the simulation image in photopic vision is generated, data of the pupil diameter of the examinee's eye in photopic vision are used. When the simulation image in twilight vision is generated, data of the pupil diameter of the examinee's eye in twilight vision are used. The photopic vision pupil diameter data and the twilight vision pupil diameter data are, for example, measured from an anterior segment image in photopic vision and an anterior segment image in scotopic vision, respectively. The examinee's eye environment that is set at the time of simulation may be set by the examiner via the input unit 40 (as will be described in detail below).

In the device according to the present embodiment, the distance between the examinee's eye and the subjective examination target, and the interval at which the corrective lens is disposed with respect to the examinee's eye that are used during simulation may be constant values or adjustable values. When these values are adjustable, values based on the correction data acquired in the process of S2 may be used, or separately acquired values (such as values input by an operation on the input unit 40) may be used.

Next, according to the flowchart of FIG. 2, a display control process (S4: display control step) is executed by the CPU 30. As a result, an eyeball model image 101, simulation images 105 and 106, and an image indicating the state of the eye optical system are displayed on the monitor 50 (see FIG. 3).

Figure 3:
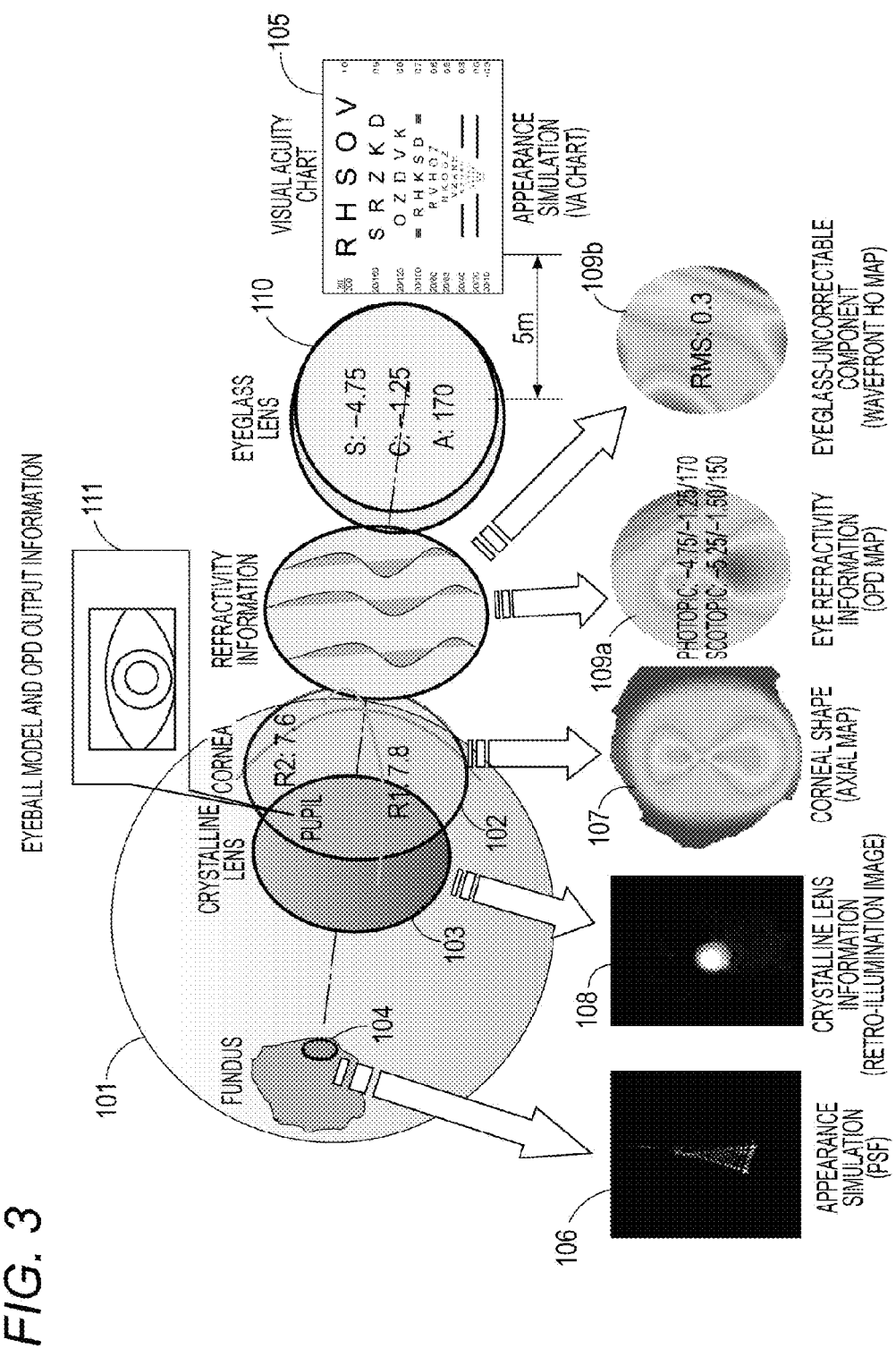
FIG. 3 illustrates examples of images displayed on a monitor as a result of execution of the ophthalmic information processing program.

The eyeball model image 101 shows the structure of the eye. In the present embodiment, as the eyeball model image 101, a schematic view showing the three-dimensional eye structure of the eyeball as seen through diagonally is used. Alternatively, as the eyeball model image 101, a cross-sectional view (or a cross-sectional schematic view) of a section perpendicular to a front-rear direction axis (such as the visual axis) may be used, for example. In FIG. 3, the eyeball model image 101 shows the overall shape of the eye. However, the eyeball model image 101 is not limited to the above, and may be set to show a partial structure of the eye. For example, the eyeball model image 101 may be an image only of an anterior segment portion including the cornea and the crystalline lens. In the present embodiment, the eyeball model image 101 has a shape (structure) that has no relationship to the actual shape of the examinee's eye. However, this is not a limitation, and the eyeball model image 101 may be formed on the basis of shape data of the examinee's eye measured by an optometry apparatus using OCT and the like.

The eyeball model image 101 shown in FIG. 3 includes a cornea graphic 102 representing the cornea at the position of the cornea. At the positions of the crystalline lens and the fundus of the eyeball model image 101, a crystalline lens graphic 103 representing the crystalline lens and a fundus graphic 104 representing the fundus are formed, respectively.

On the eyeball model image 101, information indicating the shape of the examinee's eye may be displayed. For example, in addition to the cornea curvature shown in FIG. 3, there may be shown on the eyeball model image 101 measurement values of the ocular axial length, corneal thickness, anterior chamber depth, crystalline lens thickness, vitreous body thickness, pupil diameter, and corneal diameter and the like (namely, examinee's eye size information).

The monitor 50 also displays the simulation images 105 and 106 generated by the process of S3. In the present embodiment, the first simulation image 105 showing the way the subjective examination target appears is disposed forwardly in the direction of the visual line of the eyeball model image 101 (or, when a lens graphic 110 which will be described below is disposed, even forwardly of the graphic). In the present embodiment, the second simulation image 106 showing the way the point image appears is displayed in association with the fundus of the eyeball model image 101. As shown in FIG. 3, a visual acuity chart is used as the first simulation image 105. In the visual acuity chart, a plurality of visual acuity examination targets is arranged according to eyesight values. As shown in FIG. 3, the monitor 50 may display information (numerical values and the like) indicating the distance between the subjective examination target and the examinee's eye (or, the eyeglass lens) in simulation.

As shown in FIG. 3, in the present embodiment, the first simulation image 105 and the second simulation image 106 are simultaneously displayed in the same screen by the process of S4. Thus, the examiner can simultaneously confirm an overall result of visual perception by the examinee's eye in accordance with the first simulation image, and the details of image blurriness in accordance with the second simulation image 106 (more specifically, the direction, degree, and the like of image blurriness). Accordingly, the examiner can set corrective lens prescription values easily and well. In the present embodiment, the phrase "a plurality of images is simultaneously displayed" means that a plurality of images becomes visually perceptible at once.

Also by the process of S3, both a wearing simulation image about the examinee's eye wearing a corrective lens and a non-wearing simulation image about the examinee's eye not wearing a corrective lens may be generated. In this case, in the present embodiment, a process of selectively displaying one of the in ages on the monitor 50 is performed in the process of S4. For example, the CPU 30 may be configured to select in a mode selection process which image is displayed in the process of S4.

Figure 4:
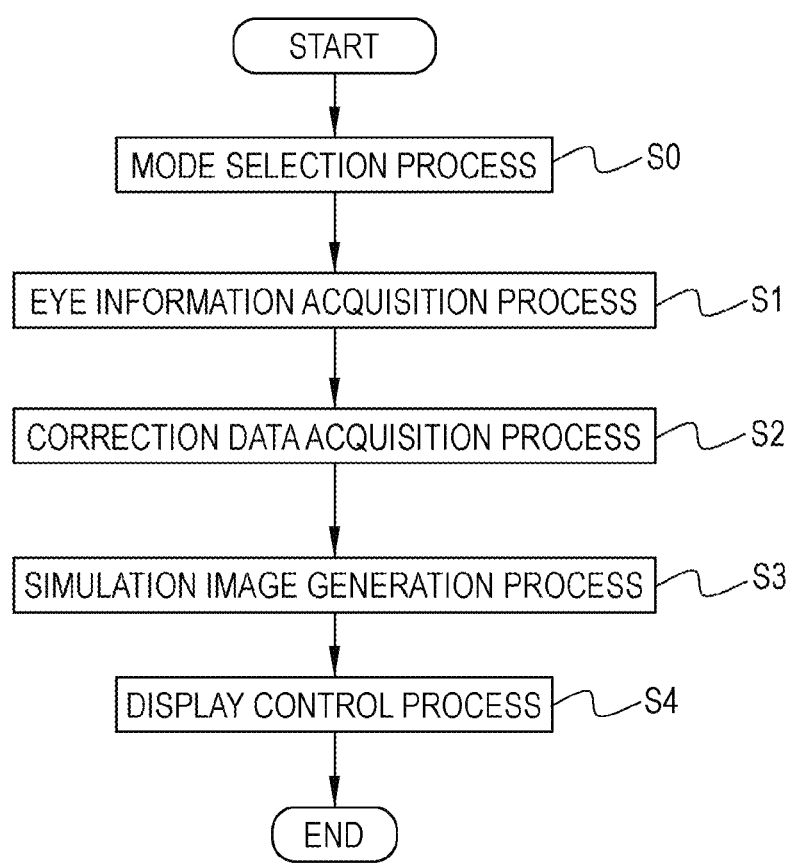
FIG. 4 is a flowchart of the flow of processing by the ophthalmic information processing program in a modification.

FIG. 4 shows a flowchart of the ophthalmic information processing program in the case where the mode selection process is performed. In the flowchart, the mode selection process (S0: mode selecting step) is shown as an initially performed process. However, this is not a limitation, and the mode selection process is only required to be performed prior to the display control process (S4).

In the mode selection process, the CPU 30 selects one display mode from a plurality of display modes. The plurality of display modes includes a first display mode in which the wearing simulation image is displayed, and a second display mode in which the non-wearing simulation image is displayed.

While the details will be described later, in the present embodiment, the selection of the display mode by the CPU 30 is performed based on an operation input on the input unit 40 (mode selection unit), for example. When the first display mode is selected by the mode selection process, the CPU 30 displays the wearing simulation image (corrected simulation image) on the monitor 50 by the process of S4. When the second display mode is selected by the mode selection process, the CPU 30 displays the non-wearing simulation in age (non-corrected simulation image) on the monitor 50 by the process of S4. The mode of display of the wearing simulation image and the non-wearing simulation image is not limited to such that one image is selectively displayed. For example, the two types of simulation images may be displayed on the same screen simultaneously.

In the process of S4, display control for modifying the distance from the eyeball model image 101 to the first simulation image 105 may be performed. For example, the CPU 30 may perform a process of moving the first simulation image 105 to a position on the monitor 50 designated by a pointing device and the like. Further, the CPU 30 may also perform a process (such as the process of S3) of generating a simulation image while the distance between the examinee's eye and the target during simulation is modified in conjunction with the distance between the eyeball model image 101 and the first simulation image 105, and the display control process (S4) for updating the simulation image on the monitor 50 to an image generated by the simulation after modification of the distance between the examinee's eye and the target. In this way, the examiner can intuitively modify the distance between the examinee's eye and the target during simulation.

In the present embodiment, the characteristics information images indicating the information about the eye optical system characteristics of the examinee's eye are displayed in association with the locations on the eyeball model image 101. In a specific example, in FIG. 3, the corneal information image 102 and the intraocular information image 103 are displayed in association with the cornea and the inside of the eyeball, respectively, of the eyeball model image 101. Further, in the present embodiment, refractivity information images 109a and 109b and an anterior segment image 111 in photopic vision or twilight vision are displayed in association with the anterior segment of the eyeball model image 101. In the processing device 1 according to the present embodiment, the respective characteristics information images are displayed in association with the locations on the eyeball model image 101. Thus, even a person not familiar with ophthalmologic imagery can easily figure out the information of which location of the examinee's eye is being indicated by each characteristics information image.

A corneal information image 107 two-dimensionally shows characteristics concerning the corneal anterior surface shape of the examinee's eye. The corneal information image 107 is generated based on the corneal information acquired by the process of S1 (such as the three-dimensional shape data, curvature data, refraction data, and aberration data of the corneal anterior surface). As the corneal information image 107, in addition to the curvature map of the corneal anterior surface shown in FIG. 3, a corneal anterior surface shape map, a refraction map (i.e., a corneal refraction map), or an aberration analysis map may be used. The refraction map shows a refractive distribution of the examinee's eye in the examination range. Particularly, the corneal refraction map shows a refractive distribution on the corneal anterior surface.

An anterior segment reflected image of a corneal shape measurement target may be used as the corneal information image 107. An example of the conical shape measurement target is a ring pattern age, such as a placido ring, projected on the examinee's eye by the anterior segment measuring apparatus 10. Further, a corneal cross-sectional image, an image showing an analysis result with respect to the corneal cross-sectional image, and the like may be used as the corneal information image 107. The corneal cross-sectional image may be an image captured by anterior segment OCT, a Scheimpflug camera, and the like, for example.

The corneal information age 107 is displayed in association with the cornea in the eyeball model image 101. Thus, even a person not familiar with ophthalmologic imagery can easily figure out that the corneal information image 107 shows the state of the cornea. For example, if a map displayed as the corneal information image 107 is disturbed, it can be inferred that there might be corneal abnormality.

An intraocular information image (crystalline lens information) 108 mainly shows characteristics concerning at least one of opacity and refraction in the examinee's eye two-dimensionally. The intraocular information image 108 is generated based on the intraocular information acquired by the process of S1. Examples of the intraocular information image 108 concerning opacity in the examinee's eye include a retro-illumination image generated based on the image data of a retro-illumination image, and an image showing an analysis result of the retro-illumination image. In the retro-illumination image, the shape of opacity in the pupil is shown. Thus, the retro-illumination image and the like can be used to confirm the presence or absence of opacity and its degree in the optic media of the examinee's eye.

The intraocular information image 108 may be a map image (such as a refraction map (i.e., an intraocular refraction map), an aberration map (i.e., an intraocular aberration map), or a high-order aberration map (i.e., an intraocular high-order aberration map)) generated based on refractivity information such as refraction data and aberration data) about the inside of the examinee's eye except for the corneal anterior surface. The intraocular refraction map shows a refractive distribution in the examinee's eye except for the corneal anterior surface. The aberration map shows a distribution of aberration caused in an examinee's eye examination range. Particularly, the intraocular aberration map shows a distribution of aberration caused in the examinee's eye except for the corneal anterior surface. The high-order aberration map is a two-dimensional map concerning a third or higher order of aberration caused in the examinee's eye examination range. Particularly, the intraocular high-order aberration map is a map concerning a third or higher order of aberration caused in the examinee's eye except for the corneal anterior surface.

The intraocular refraction map (which is an example of the intraocular refractivity information image) may be obtained by using, for example, a differential between the refractive distribution in the examinee's eye as a whole and the refractive distribution in the corneal anterior surface (see JP-A-2006-26242 for more detail). The intraocular refractivity information image is an image concerning the refractive distribution corresponding to refraction in the examinee's eye except for the corneal anterior surface, and is an example of the intraocular information image 108.

The intraocular information image 108 is displayed in association with the inside of the eyeball in the eyeball model image 101. Thus, even a person not familiar with ophthalmologic imagery can easily figure out that the intraocular information image 108 shows the state inside the eyeball. Particularly, in the present embodiment, as shown in FIG. 3, the intraocular information image 108 is displayed in association with the crystalline lens in the eyeball model image 101. The crystalline lens is a typical location where opacity or refractive error may be caused in the eye. Accordingly, even a person not familiar with ophthalmologic imagery can easily figure out that the intraocular information image 108 has a strong relationship with the state of the crystalline lens in particular.

When an unclear target image is formed in the simulation images 105 and 106, it may be difficult to identify the cause of the unclear target image from the content of the corneal information image 107. In this case, the cause of the unclear target image may be shown in the content of the intraocular information image 108. For example, if the intraocular information image 108 shows that there is opacity in the examinee's eye, it may be inferred that unclarity may remain in the target image even if the refractive error of the examinee's eye is corrected. Also, if the intraocular information image 108 shows a disturbed refractive distribution, for example, it can be inferred that irregular astigmatism and the like due to refractive error in the examinee's eye may be the cause of the unclear target image.

The refractivity information image 109 also two-dimensionally shows characteristics concerning refraction of the examinee's eye as a whole in the examination range. The refractivity information image 109 is generated based on the refractivity information of the examinee's eye as a whole (such as refraction data and aberration data) acquired by of the process of S1. The mode of the refractivity information image 109 includes, for example, a total eye refraction map, a wavefront map, an eyeglass-uncorrectable component map, and a Shack-Hartmann image. The refractivity information image 109 shows the state of refraction of the examinee's eye as a whole (entire examinee's eye). The total eye refraction map shows a refractive distribution of the examinee's eye as a whole in the examination range.

A total eye refraction map 109a, which is a mode of the refractivity information image 109, shows the distribution of refraction of the examinee's eye as a whole. An eyeglass-uncorrectable component map 109b, which is another mode of the refractivity information image 109, shows a distribution of a high-order (third order or higher) aberration in the examination range. As shown in FIG. 3, the refractivity information image 109 may have various values attached concerning the refractive power of the examinee's eye. For example, a value indicating the refractive power of the examinee's eye may be attached to the refractivity information image 109 (see the map 109a). For example, values of S, C, and A may be displayed. The pupil diameter may also be displayed in the refractivity information image 109. The value indicating refraction and the pupil diameter may be displayed for each of the case of photopic vision and the case of twilight vision. There may also be attached information of values indicating the magnitude of the uncorrectable component (such as the amount of high-order aberration and an RMS (the root-mean-sum of a measurement value error with respect to an approximation curve of dioptre in the circumference direction) (see the map 109b).

In FIG. 3, the total eye refraction map 109a and the eyeglass-uncorrectable component map 109b are simultaneously displayed. However, the process of S4 may be such that only one of the images is displayed.

The anterior segment image 111 shows at least the size of the pupil in the simulation environment. In the present embodiment, when a simulation image in photopic vision is displayed, the anterior segment image 111 in photopic vision is displayed. When a simulation image in twilight vision is displayed, the anterior segment image 111 in twilight vision is displayed. In the anterior segment image 111, a measurement value of the pupil diameter may be additionally displayed.

The processing device 1 may be configured to switch the simulation image and the anterior segment image 111 displayed on the monitor between those concerning photopic vision and those concerning twilight vision. More specifically, the processing device 1 may be configured such that, when an image in one of the environments of photopic vision and twilight vision is being displayed, the displayed image is switched to the image in the other environment on the basis of the input of a display switch signal to the processing device 1. The display switch signal may be output through a predetermined operation with respect to the input unit 40, such as selecting the simulation image or the anterior segment image 111 on the screen using a pointing device and the like.

In order to express the correspondence between the location of the eyeball model image 101 and the characteristics information image, various display techniques may be used. For example, the correspondence may be expressed by placing the characteristics information image in proximity to a corresponding location of the eyeball model image 101. Alternatively, the correspondence may be expressed by superposing the characteristics information image over a corresponding location of the eyeball model image 101. It is also possible to use a symbol (i.e., a corresponding graphic, such as a line, an arrow, or a balloon) indicating the correspondence between the characteristics information image and the eyeball model image 101.

For example, a plurality of characteristics information images associated with various locations on the eyeball model image may be displayed in an arrangement corresponding to the arrangement of the various locations of the examinee's eye in the eyeball model image. When a graphic (such as the graphics 102 to 104) is selected by the operation of the pointing device and the like, the mode of display of the characteristics information image corresponding to the selected location on the eyeball model image 101 may be modified to denote their correspondence. For example, when a graphic on the eyeball model is selected, the characteristics information image corresponding to the selected location is emphasized by an increase in size or blinking, or a characteristics information image that has been set for non-display in advance may be pop-up displayed.

The display control process (S4) according to the present embodiment may include a process of switching the mode of at least one image among the characteristics information images being displayed on the screen of the monitor 50. For example, as the intraocular information image 108, an image showing the opacity distribution of the crystalline lens (such as a retro-illumination image) is displayed. In this case, the intraocular information image 108 may be snitched to another mode of display, such as a crystalline lens refraction map. The selection of the image of which the display mode is switched may be performed by the CPU 30 on the basis of an operation input to the input unit 40. A specific example of the operation input is placing the cursor of a pointing device over the characteristics information image. When the characteristics information image of which the display mode is to be switched is designated, the display control process (S4) may cause the display of a list of index information (such as image names and thumbnail images) of candidates of display modes after the switching. In this case, the CPU 30 causes the characteristics information image selected by the examiner from among the candidates to be newly displayed. The examiner may make a selecting input via the input unit 40.

Further, as shown in FIG. 3, in the display control process (S4) according to the present embodiment, the CPU 30 causes a lens graphic 110 representing a corrective lens (in FIG. 3, an eyeglass lens) to be displayed forwardly of the examinee's eye.

In the present embodiment, the display control process (S4) includes a process of controlling the display mode of the lens graphic 110 on the monitor 50 to one of a mode denoting the wearing of the eyeglass lens with respect to the eyeball of the eyeball model image 101, and a mode denoting the non-wearing of the eyeglass lens with respect to the eyeball of the eyeball model image 101. For example, the location of the lens graphic 110 may be varied between the mode denoting the wearing of the eyeglass lens and the mode denoting the non-wearing of the eyeglass lens. More specifically, as shown in FIG. 3, the wearing of the eyeglass lens may be denoted by locating the lens graphic 110 at a forward position (such as the lens fit position) in the direction of the visual line of the eyeball of the eyeball model image 101. On the other hand, the non-wearing of the eyeglass lens may be denoted by locating the lens graphic 110 at a position spaced apart from the visual line of the eyeball of the eyeball model image 101, or by not displaying the lens graphic 110. Further, the degree of emphasis of the lens graphic 110 may be varied between the mode denoting the wearing of the eyeglass lens and the mode denoting the non-wearing of the eyeglass lens. For example, when denoting the wearing of the eyeglass lens, the lens graphic 110 may be emphasized more than when denoting the non-wearing of the eyeglass lens. The emphasized display includes, for example, increasing the contrast of the lens graphic 110, and increasing the thickness of the edge line of the lens graphic 110.

In the present embodiment, the CPU so selects the display mode of the lens graphic 110 on the basis of the common operation input to the operation for selecting the above-described simulation image display mode. Thus, when the wearing simulation image is displayed in the first display mode, the lens graphic 110 denoting the wearing of the eyeglass lens is simultaneously displayed on the monitor 50. On the other hand, when the non-wearing simulation image is displayed in the second display mode, the display mode of the lens graphic 110 on the monitor 50 becomes the non-wearing denoting mode. In this way, according to the present embodiment, the lens graphic 110 display mode and the simulation image display mode are switched in conjunction with each other. Accordingly, the processing device 1 allows the examiner to readily figure out, based on the lens graphic 110 display mode, whether the wearing simulation image or the non-wearing simulation image is being displayed on the monitor 50.

Further, in the present embodiment, when the correction data used for simulation is not acquired in the process of S2, the lens graphic 110 may not be displayed. Obviously, the lens graphic 110 may be displayed regardless of whether the correction data is acquired. As shown in FIG. 3, the correction data, such as prescription values, may be displayed together with the lens graphic 110.

The display control process (S4) may also include a process of rotating a graphic related to the cylindrical axis of the lens (such as a lens graphic per se, or the cylindrical axis on the lens graphic) in the lens graphic 110. For example, when the examiner designates the orientation of the cylindrical axis (cylindrical axis angle) after movement using a pointing device, the graphic related to the cylindrical axis may be moved. The processing device 1 may also be configured to modify, during simulation, the correction data concerning the cylindrical axis in conjunction with the rotation of the graphic related to the cylindrical axis. Thus, the CPU 30 may perform, for example, a process of newly generating the simulation images 105 and 106 on the basis of the correction data of the designated cylindrical axis angle, and a process of updating the simulation image on the monitor to the newly generated images while rotating the graphic related to the cylindrical axis. The examiner, for example, can confirm the simulation images 105 and 106 with the modified lens cylindrical axis through the operation of rotating the graphic related to the cylindrical axis. This function is particularly useful when, for example, examining correction data having a proper cylindrical axis by simulation with regard to the examinee's eye of which the astigmatic axial angle is varied between photopic vision and twilight vision.

The process of S4 may include display control for modifying the distance from the eyeball model image 101 to the lens graphic 110 in the display mode denoting the wearing of the eyeglass lens. Further, the CPU 30 may perform a process of generating the simulation image while modifying the interval of the examinee's eye and the location of the corrective lens during simulation in conjunction with the distance between the eyeball model image 101 and the lens graphic 110 (such as the process of S3), and the display control process (S4) of updating the simulation image on the monitor 50 to the simulation image generated using the modified distance between the examinee's eye and the corrective lens. The monitor 50 may also display information (such as numerical values) indicating the interval of the examinee's eye and the location of the corrective lens during simulation.

It may be difficult to know whether a state of a proper lens being prescribed is being simulated just by looking at the simulation image. One reason is that, when the examinee's eye has irregular astigmatism, the image may be blurred even if refraction of the examinee's eye is properly corrected. In this regard, the CPU 30 of the processing device 1 according to the present embodiment causes the characteristics information images concerning the characteristics of various locations of the examinee's eye to be displayed in association with the locations on the eyeball model image 101. Thus, even a person not familiar with ophthalmologic imagery can readily know the information about which location of the examinee's eye is being shown by each characteristics information image. Further, the characteristics information image and the eyeball model image 101 are displayed together with the simulation images 105 and 106. Thus, when the simulation image is unclear, for example, the examiner can readily intuitively know the reason from the characteristics information image.

The technology according to the present disclosure has been described with reference to embodiments. The technology of the present disclosure is not limited to the embodiments and may be variously modified. For example, in the embodiments, the first simulation image 105 and the second simulation image 106 are simultaneously displayed on the same screen. Alternatively, the processing device 1 may be configured to display only one of the two types of simulation images.

The embodiments of the present disclosure may include a first to a sixteenth ophthalmic image processing methods and a first storage medium as follows.

The first ophthalmic image processing method is an ophthalmic image processing method for displaying examinee's eye characteristics obtained by an optometry apparatus, the method including performing, in an ophthalmic information processing device, an acquisition step of acquiring information about the characteristics of the examinee's eye including at least corneal information about the anterior surface shape of the cornea of the examinee's eye, and refractivity information about refraction of the examinee's eye as a whole; a generating step of generating a simulation image of a target image that is formed at the fundus of the examinee's eye, using at least the refractivity information obtained in the acquisition step; and a display control step of causing an eyeball model image showing an eyeball structure and the simulation image obtained in the generating step to be simultaneously displayed on a display device, and further causing a corneal information image based on the corneal information obtained in the acquisition step to be simultaneously displayed on the display device in association with the cornea on the eyeball model image.

The second ophthalmic image processing method is the first ophthalmic image processing method wherein the acquisition step further includes acquiring intraocular information about at least one of opacity in the examinee's eye and refraction in the examinee's eye except for the corneal anterior surface, and wherein the display control step further includes causing an intraocular information image based on the intraocular information obtained in the acquisition step to be displayed on the display device in association with the inside of the eyeball on the eyeball model image and simultaneously with the eyeball model image, the simulation image, and the corneal information image.

The third ophthalmic image processing method is the second ophthalmic image processing method wherein the acquisition step includes acquiring, as the intraocular information about the opacity in the examinees eye, at least a retro-illumination image of the examinee's eye, and the display control step includes causing the retro-illumination image obtained in the acquisition step to be displayed as the intraocular information image.

The fourth ophthalmic image processing method is the second ophthalmic image processing method wherein the acquisition step includes acquiring, as the intraocular information, at least the intraocular information about refraction in the examinee's eye except for the corneal anterior surface, and the display control step includes causing an intraocular refractivity information image concerning a refractive distribution based on the intraocular information to be displayed as the intraocular information image.

The fifth ophthalmic image processing method is the fourth ophthalmic image processing method wherein the display control step includes causing a corneal refraction map showing the refractive distribution on the corneal anterior surface to be displayed as the corneal information image based on the corneal information, and further causing an intraocular refraction map which is a refraction map of the inside of the examinee's eye except for the cornea to be displayed as the intraocular refractivity information image.

The sixth ophthalmic image processing method is the first ophthalmic image processing method further including performing a correction data acquisition step of acquiring correction data of a corrective lens for correcting the refractive error of the examinee's eye, wherein the generating step includes generating a wearing simulation image which is the simulation image of the target image formed at the fundus of the examinee's eye in a corrective lens wearing state, using at least the refractivity information and the correction data.

The seventh ophthalmic image processing method is the sixth ophthalmic image processing method including a mode selecting step of selecting one display mode from a plurality of display modes including a first display mode for displaying the simulation image with respect to the examinee's eye wearing a corrective lens and a second display mode for displaying the simulation image with respect to the examinee's eye not wearing a corrective lens, wherein the generating step includes generating the corrected simulation image and a non-wearing simulation image which is a simulation image with respect to the examinee's eye not wearing a corrective lens, wherein the display control step includes causing, when the first display mode is selected in the mode selecting step, the corrected simulation image to be displayed on the display device simultaneously with the eyeball model image, the simulation image, and the corneal information image, or, when the second display mode is selected in the mode selecting step, causing the non-corrected simulation image to be displayed on the display device simultaneously with the eyeball model image, the simulation image, and the corneal information image.

The eighth ophthalmic image processing method is the seventh ophthalmic image processing method wherein the display control step includes causing a lens graphic representing the corrective lens to be displayed at a lens fit position in the eyeball model image simultaneously with the wearing simulation image.

The ninth ophthalmic image processing method is the first ophthalmic image processing method wherein the display control step includes causing a refractivity information image which is a refractivity information image based on the refractivity information and which concerns a refractive distribution of the examinee's eye as a whole in the examination range to be displayed on the display device simultaneously with the eyeball model image, the simulation image, and the corneal information image.

The tenth ophthalmic image processing method is the ninth ophthalmic image processing method wherein the display control step includes causing an aberration map showing a distribution of aberration caused in the examination range of the examinee's eye to be displayed on the display device as the refractivity information image.

The eleventh ophthalmic image processing method is the tenth ophthalmic image processing method wherein the display control step includes causing a high-order aberration map which is a two-dimensional map concerning a third or higher order of aberration caused in the examination range of the examinee's eye to be displayed on the display device.

The twelfth ophthalmic image processing method is the ninth ophthalmic image processing method wherein the display control step includes causing a total eye refraction map showing a distribution of refraction of the examinee's eye as a whole in the examination range to be displayed on the display device as the refractivity information image.

The thirteenth ophthalmic image processing method is the first ophthalmic image processing method wherein the generating step includes generating, as the simulation image, a first simulation image simulated with regard to a first target which is a subjective examination target, and a second simulation image simulated with regard to a second target which is a point image, and wherein the display control step includes causing the first simulation image and the second simulation image to be displayed on the display device simultaneously with the eyeball model image, the simulation image, and the corneal information image.

The fourteenth ophthalmic image processing method is the first ophthalmic image processing method wherein the generating step includes generating a simulation image in photopic vision based on data of a pupil diameter of the examinee's eye in photopic vision, and a simulation image in twilight vision based on data of the pupil diameter of the examinee's eye in twilight vision, and wherein the display control step includes causing the anterior segment image of the examinee's eye in photopic vision to be displayed simultaneously with the simulation image in photopic vision in association with the anterior segment of the eyeball model image, and causing the anterior segment image of the examinee's eye in twilight vision to be displayed simultaneously with the simulation image in twilight vision in association with the anterior segment of the eyeball model image.

The fifteenth ophthalmic image processing method is the first ophthalmic image processing method wherein the display control step includes causing a corresponding graphic for indicating a correspondence relationship between various locations of the eyeball model image and images associated with the various locations on the eyeball model image to be displayed on the display device simultaneously with the eyeball model image, the simulation image, and the corneal information image.

The sixteenth ophthalmic image processing method is the first ophthalmic image processing method wherein the display control step includes causing images associated with various locations on the eyeball model image to be displayed on the display device in an arrangement corresponding to an arrangement of various locations of the examinee's eye in the eyeball model image.

The first storage medium is a storage medium having an ophthalmic information processing program for displaying examinee's eye characteristics obtained by an optometry apparatus stored therein, the ophthalmic information processing program, when executed by a processor of the ophthalmic information processing device, causing the ophthalmic information processing device to perform an acquisition step of acquiring information about the characteristics of the examinee's eye including at least corneal information about an anterior surface shape of the cornea of the examinee's eye, and refractivity information about refraction of the examinee's eye as a whole; a generating step of generating a simulation image of a target image that is formed at the fundus of the examinee's eye, using at least the refractivity information obtained in the acquisition step; and a display control step of causing an eyeball model image showing an eyeball structure and the simulation image obtained in the generating step to be simultaneously displayed on a display device, and further causing a corneal information image based on the corneal information obtained in the acquisition step to be simultaneously displayed on the display device in association with the cornea on the eyeball model image.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmic image processing method comprising:
    acquiring information about characteristics of an examinee's eye including corneal information about the corneal anterior surface shape of the examinee's eye, and refractivity information about refraction of the examinee's eye as a whole;
    generating a simulation image of a target image formed at fundus of the examinee's eye using the refractivity information; and
    simultaneously displaying an eyeball model image showing an eyeball structure, the simulation image, and a corneal information image associated with the cornea on the eyeball model image and corresponding to the corneal information.

2. The ophthalmic image processing method according to claim 1, comprising:
    acquiring intraocular information about at least one of opacity in the examinee's eye and refraction in the examinee's eye except for the corneal anterior surface; and
    displaying an intraocular information image corresponding to the intraocular information in association with the inside of the eyeball of the eyeball model image simultaneously with the eyeball model image, the simulation image, and the corneal information image.

3. The eye ophthalmic image processing method according to claim 2, comprising:
    acquiring a retro-illumination image of the examinee's eye as the intraocular information about the opacity in the examinee's eye; and
    displaying the retro-illumination image as the intraocular information image.

4. The ophthalmic image processing method according to claim 2, comprising:
    acquiring at least intraocular information about refraction in the examinee's eye except for the corneal anterior surface as the intraocular information; and
    displaying an intraocular refractivity information image concerning a refractive distribution corresponding to the intraocular information as the intraocular information image.

5. The ophthalmic image processing method according to claim 4, comprising:
    displaying a corneal refraction map indicating a refractive distribution on the corneal anterior surface as the corneal information image corresponding to the corneal information; and displaying an intraocular refraction map that is a refraction map of the inside of the examinee's eye except for the co ea as the intraocular refractivity information image.

6. The ophthalmic image processing method according to claim 1, further comprising:
    acquiring correction data for a corrective lens for correcting a refractive error of the examinee's eye; and
    generating a wearing simulation image that is a simulation image of the target image formed at the fundus of the examinee's eye wearing the corrective lens, using the refractivity information and the correction data.

7. The ophthalmic image processing method according to claim 6, further comprising:
    selecting one display mode from a plurality of display modes including a first display mode for displaying the wearing simulation image, and a second display mode for displaying a non-wearing simulation image that is a simulation image with respect to the examinee's eye not wearing the corrective lens;
    generating the wearing simulation image and the non-wearing simulation image; and
    displaying the wearing simulation image simultaneously with the eyeball model image, the simulation image, and the corneal information image when the first display mode is selected, or displaying the non-wearing simulation image simultaneously with the eyeball model image, the simulation image, and the corneal information image when the second display mode is selected.

8. The ophthalmic image processing method according to claim 7, comprising displaying a lens graphic representing the corrective lens at a lens fit position in the eyeball model image simultaneously with the wearing simulation image.

9. The ophthalmic image processing method according to claim 1, comprising displaying a refractivity information image concerning a distribution of refraction of the examinee's eye as a whole in the examination range and based on the refractivity information, simultaneously with the eyeball model image, the simulation image, and the corneal information image.

10. The ophthalmic image processing method according to claim 9, comprising displaying an aberration map showing a distribution of aberration caused in the examination range of the examinee's eye as the refractivity information image.

11. The ophthalmic image processing method according to claim 10, comprising displaying a high-order aberration map that is a two-dimensional map concerning a third or higher order of aberration caused in the examination range of the examinee's eye.

12. The ophthalmic image processing method according to claim 9, comprising displaying a total eye refraction map indicating a distribution of refraction of the examinee's eye as a whole in the examination range as the refractivity information image.

13. The ophthalmic image processing method according to claim 1, comprising:
    generating, as the simulation image, a first simulation image obtained by simulation using a first target that is a subjective examination target and a second simulation image obtained by simulation using a second target that is a point image; and
    displaying the first simulation image and the second simulation image simultaneously with the eyeball model image, the simulation image, and the corneal information image.

14. The ophthalmic image processing method according to claim 1, comprising:
    generating the simulation image in photopic vision based on data of a pupil diameter of the examinee's eye in photopic vision, and a simulation image in twilight vision based on the data of the pupil diameter of the examinee's eye in twilight vision; and
    displaying the simulation image in photopic vision and the anterior segment image of the examinee's eye in photopic vision in association with the anterior segment of the eyeball model image, and displaying the simulation image in twilight vision and the anterior segment image of the examinee's eye in twilight vision in association with the anterior segment of the eyeball model image.

15. The ophthalmic image processing method according to claim 1, comprising displaying a corresponding graphic for indicating a correspondence relationship between various locations of the eyeball model image and images associated with the various locations of the eyeball model image simultaneously with the eyeball model image, the simulation image, and the corneal information image.

16. The ophthalmic image processing method according to claim 1, comprising displaying images associated with various locations of the eyeball model image in an arrangement corresponding to an arrangement of various locations of the examinee's eye in the eyeball model image.

17. A non-transitory storage medium having a computer program for causing a computer to function as an ophthalmic information processing device stored therein, the ophthalmic information processing device performing:
    acquiring information about the characteristics of an examinee's eye including corneal information about a corneal anterior surface shape of the examinee's eye and refractivity information about refraction of the examinee's eye as a whole;
    generating a simulation image of a target image formed at the fundus of the examinee's eye using the refractivity information; and
    simultaneously displaying an eyeball model image showing an eyeball structure, the simulation image, and a corneal information image associated with the cornea on the eyeball model image and corresponding to the conical information.

* * * * *